United States Patent
Van Es

(10) Patent No.: US 6,375,353 B1
(45) Date of Patent: Apr. 23, 2002

(54) X-RAY DEVICE

(75) Inventor: Arthur R. Van Es, Eindhoven (NL)

(73) Assignee: U.S. Philips Corporation, New York, NY (US)

( * ) Notice: Subject to any disclaimer, the term of this patent is extended or adjusted under 35 U.S.C. 154(b) by 0 days.

(21) Appl. No.: 09/460,933

(22) Filed: Dec. 14, 1999

(30) Foreign Application Priority Data

Dec. 14, 1998 (EP) .............................................. 98204239

(51) Int. Cl.$^7$ ................................................. H05G 1/02
(52) U.S. Cl. ....................... 378/197; 378/195; 378/196; 378/198
(58) Field of Search ................................ 378/195, 196, 378/197, 198

(56) References Cited

U.S. PATENT DOCUMENTS 2,818,510 A * 12/1957 Verse
3,281,598 A * 10/1966 Hollstein
4,955,046 A * 9/1990 Siczek et al.
5,410,584 A * 4/1995 Schaefer et al.

FOREIGN PATENT DOCUMENTS

JP 2249533 10/1990

* cited by examiner

Primary Examiner—Robert H. Kim
Assistant Examiner—Courtney Thomas
(74) Attorney, Agent, or Firm—John F. Vodopia

(57) ABSTRACT

An X-ray device includes a C-shaped arm, a first end of which supports an X-ray source and a second end of which supports an X-ray image pick-up device. The C-shaped arm is pivotable about a pivot axis relative to a carriage. The carriage is tiltable about a tilting axis relative to a guide. The guide is rotatable about a propeller axis. The tilting axis extends at an angle relative to the propeller axis. A leverage point on the propeller axis is situated near the tilting axis. The mass center of the C-shaped arm is situated on the pivot axis. The mass centers of the C-shaped arm and of the carriage are situated on a leverage line which extends at least substantially through the leverage point. The mass centers of the C-shaped arm and of the carriage are situated to both sides of the leverage point. The ratio of the distance between the mass center of the C-shaped arm and the leverage point to the distance between the mass center of the carriage and the leverage point is substantially equal to the ratio of the mass of the carriage to the mass of the C-shaped arm.

11 Claims, 5 Drawing Sheets

X-RAY DEVICE

BACKGROUND OF THE INVENTION

1. Field of the Invention

The invention relates to an X-ray device, including a C-shaped arm, a first end of which supports an X-ray source and a second end of which supports an X-ray image pick-up device, a carriage which supports the C-shaped arm so that it is pivotable about a pivot axis, and a guide which supports the carriage so that it is tiltable about a tilting axis.

2. Description of Related Art

In such an X-ray device which is known from Japanese patent application JP-2-249533, the C-shaped arm is pivotable relative to the carriage and the carriage is tiltable relative to the guide. The pivot axis and the tilting axis therein extend parallel to one another. Because the carriage is tiltable relative to the guide, the pivoting motion to be performed by the C-shaped arm is greater than if the carriage were rigidly connected to the guide. Before an X-ray exposure can take place, the C-shaped arm and the carriage are locked, using electromagnetic or mechanical locks, in the desired position relative to the carriage and to the guide, respectively. If locking is omitted, the C-shaped arm and/or the carriage will start to pivot or be tilted until the respective mass centers of the C-shaped arm and the carriage are situated in an as low as possible position. Locking is a comparatively time-consuming operation and the electromagnetic or mechanical means required for locking have a comparatively complex and expensive construction. If locking is to be performed manually, there is a risk that the operator forgets to lock the device, so that the C-shaped arm and/or the carriage start to perform an undesirable and possibly risky pivoting and/or tilting motion.

Citation of a reference herein, or throughout this specification, is not to construed as an admission that such reference is prior art to the Applicant's invention of the invention subsequently claimed.

SUMMARY OF THE INVENTION

It is an object of the invention to provide an X-ray device in which the C-shaped arm and the carriage remain in any pivoted and/or tilted position also without being locked.

This object is achieved in the X-ray device according to the invention in that the guide is rotatable about a propeller axis, the tilting axis extending at an angle relative to the propeller axis, a leverage point on the propeller axis being situated near the tilting axis, the mass center of the C-shaped arm being situated on the pivot axis, the mass centers of the C-shaped arm and of the carriage being situated on a leverage line which extends at least substantially through the leverage point, the mass centers of the C-shaped arm and of the carriage being situated to both sides of the leverage point and the ratio of the distance between the mass center of the C-shaped arm and the leverage point to the distance between the mass center of the carriage and the leverage point being substantially equal to the ratio of the mass of the carriage to the mass of the C-shaped arm.

Because the mass center of the C-shaped arm is situated on the pivot axis, the position of the mass center of the C-shaped arm relative to the slide remains constant. Because of the ratios of the distances between the mass centers and the leverage point and the ratios of the masses, the turning moment exerted around the propeller axis by the weight of the C-shaped arm will be compensated in any position by the turning moment exerted around the propeller axis by the weight of the carriage.

Consequently, the C-shaped arm and the carriage need not be locked and can be pivoted and tilted simply by hand. Because locks and drives are not necessary for the C-shaped arm and the carriage, the X-ray device according to the invention may have a comparatively simple, compact and economical construction.

Because of the friction present between the C-shaped arm and the carriage and between the carriage and the guide, the leverage point need not be situated exactly on the leverage line and on the tilting axis. The less friction occurs between the C-shaped arm, the carriage and the guide, the more critical the position of the leverage point and the ratio of the distances and the masses will be.

Therefore, in an embodiment according to the invention the leverage point is situated on the tilting axis and the leverage line. If the ratio of the distances is substantially equal to the ratio of the masses, the C-shaped arm and the carriage will remain in any pivoted and tilted position without locking, even if the friction in X-ray device is comparatively low.

The invention will be described in detail hereinafter with reference to the drawings; therein:

BRIEF DESCRIPTION OF THE DRAWING

Corresponding parts are denoted by corresponding reference numerals in the Figures.

DETAILED DESCRIPTION OF THE PREFERRED EMBODIMENTS

Figure 1:
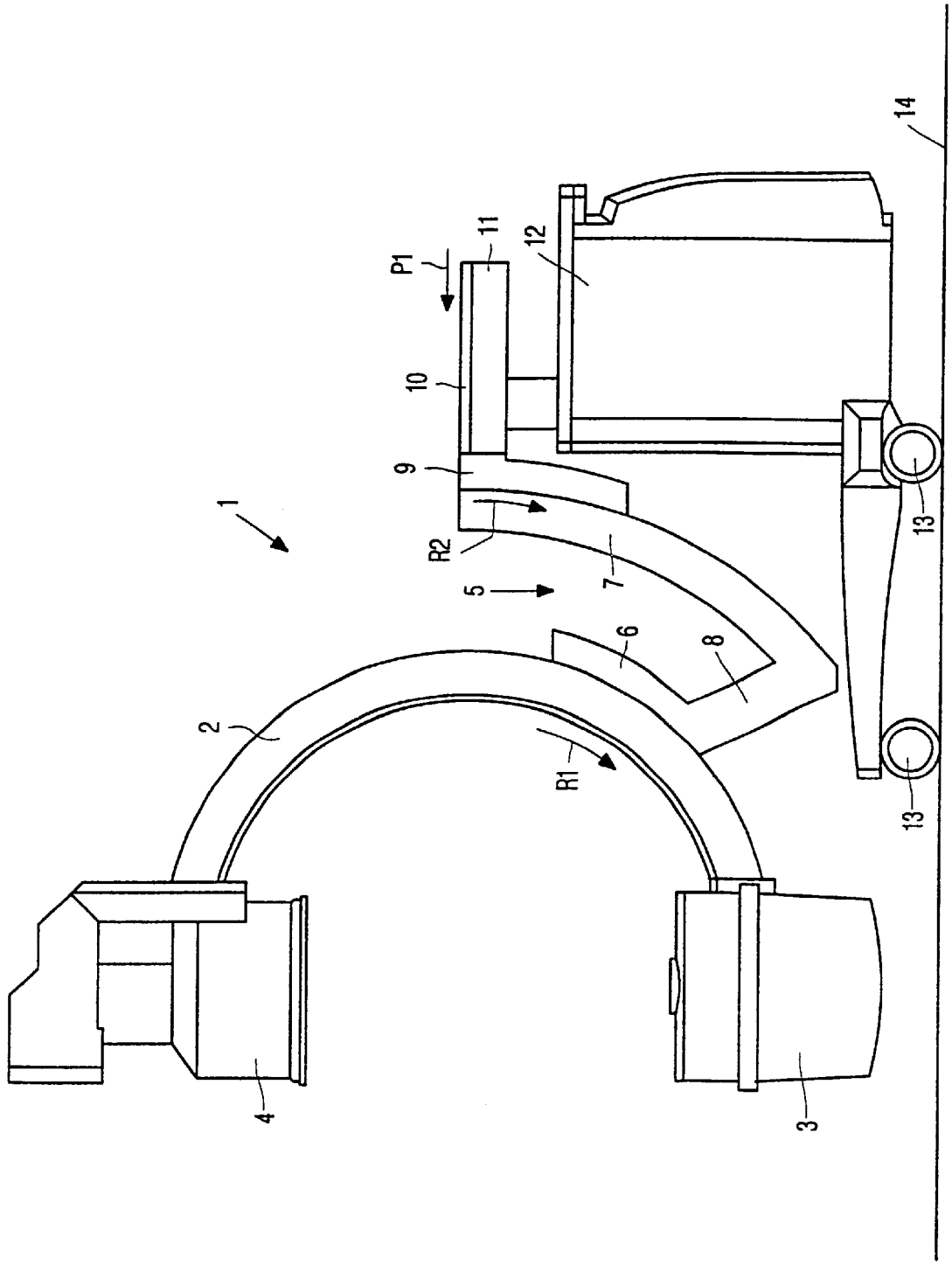
FIGS. 1 to 3 are side elevations of an X-ray device according to the invention in various pivoted and tilted positions.
Figure 2:
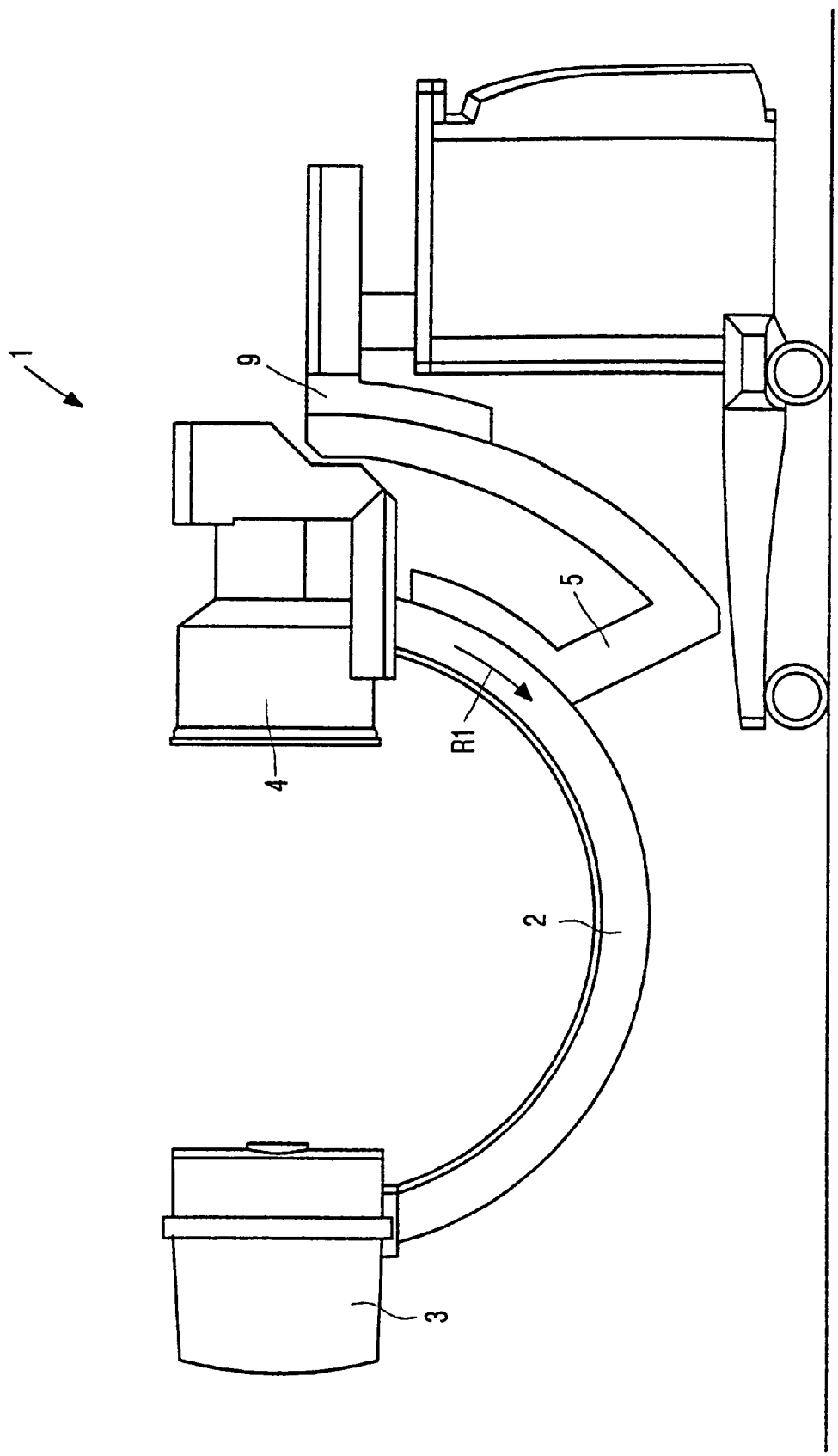
Figure 3:
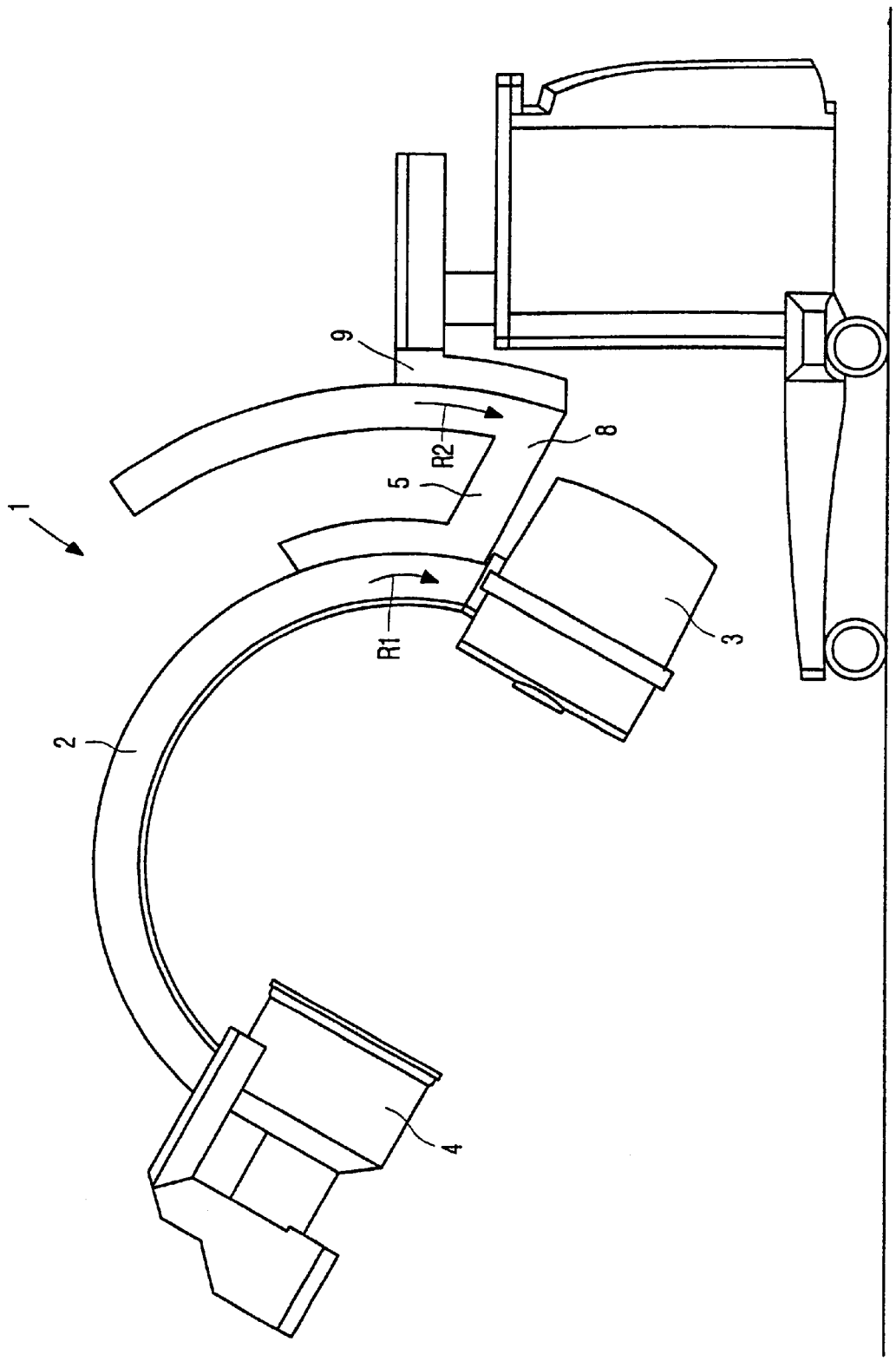

The FIGS. 1 to 3 are side elevations of an X-ray device 1 according to the invention which is provided with a C-shaped arm 2, a first end of which supports an X-ray source 3 whereas a second end thereof supports an image X-ray image pick-up device 4. The C-shaped arm 2 is journaled so as to be pivotable relative to a carriage 5. The carriage 5 is provided with two segmental arcs 6, 7 which are interconnected by way of a bridge portion 8.

The C-shaped arm 2 is journaled so as to be pivotable, relative to the segmental arc 6, in the direction of the arrow RI and in the opposite direction. The segmental arc 7 is journaled so as to be tiltable, relative to a guide 9, in the direction of the arrow R2 and in the opposite direction. The guide 9 is rotatable about a propeller axis which extends horizontally (see the FIG. 4 and 5). The guide 9 is also provided with a strip 10 which is displaceable, relative to a bearing block 11, in the direction of the arrow P1 and in the opposite direction. The bearing block 11 is connected to a box-like frame 12 so as to be rotatable about a vertically extending axis; this frame is displaceable on a substrate 14 by way of wheels 13.

In the X-ray device 1 as shown in FIG. 1 the carriage 5 occupies a lowermost position whereas the C-shaped arm 2 is situated so that the X-ray source 3 and the X-ray image pick-up device 4 are situated vertically one above the other.

In FIG. 2 the C-shaped arm 2 has been pivoted, relative to the position shown in FIG. 1, in the direction indicated by the arrow RI to such an extent that the X-ray source 3 and the X-ray image pick-up device 4 are situated horizontally opposite one another.

In the position of the X-ray device 1 as shown in FIG. 3, the carriage 5 has been rotated, in a direction opposing the arrow R2, to a maximum attainable uppermost position. The C-shaped arm 2 has been pivoted, relative to the slide 5, in a direction opposing the arrow R1 to such an extent that the X-ray source 3 is situated near the bridge portion 8 of the carriage 5.

Figure 4:
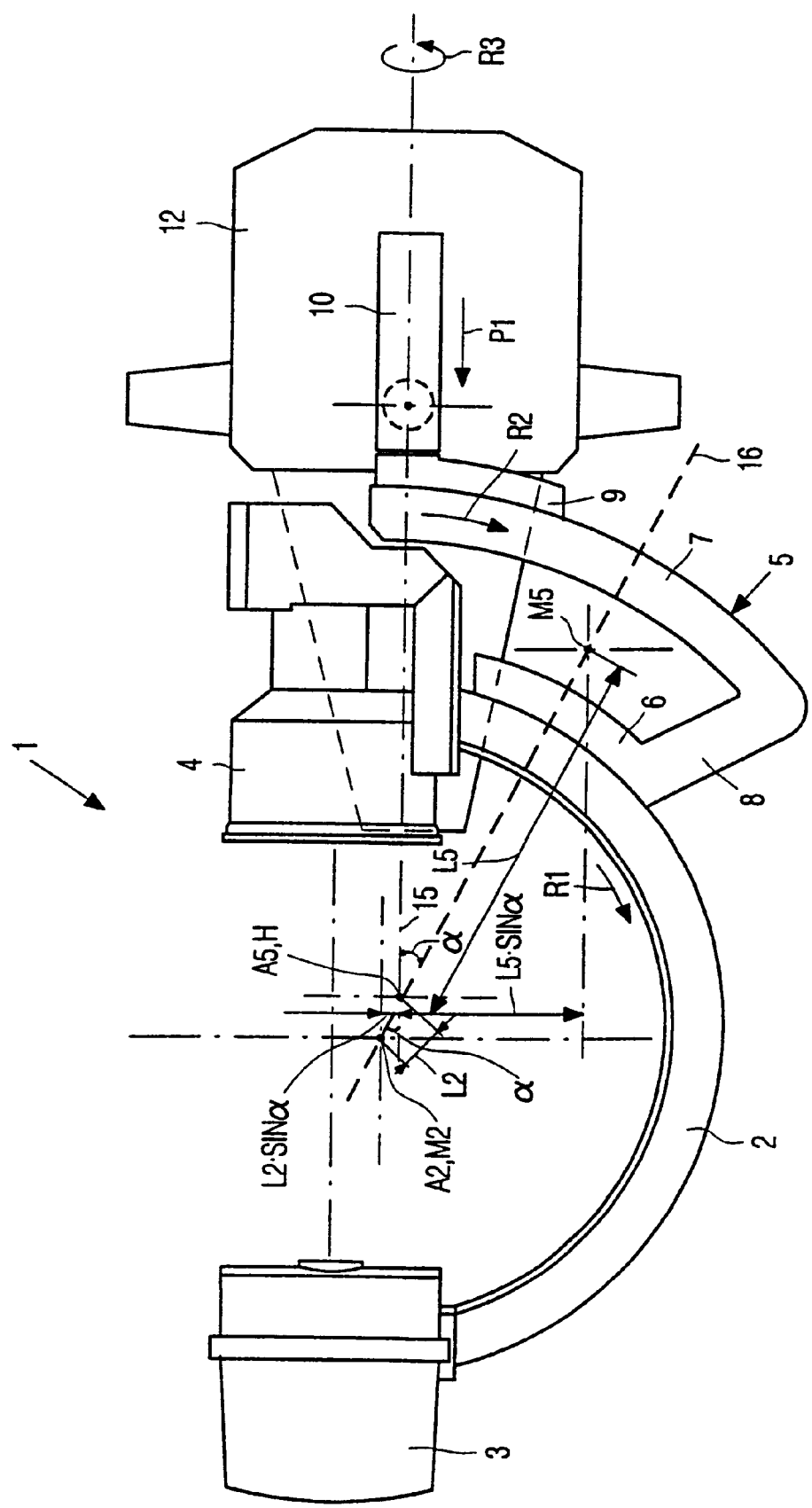
FIGS. 4 and 5 are plan views, taken in other pivoted and tilted positions, of the X-ray device shown in the FIGS. 1 to 3.
Figure 5:
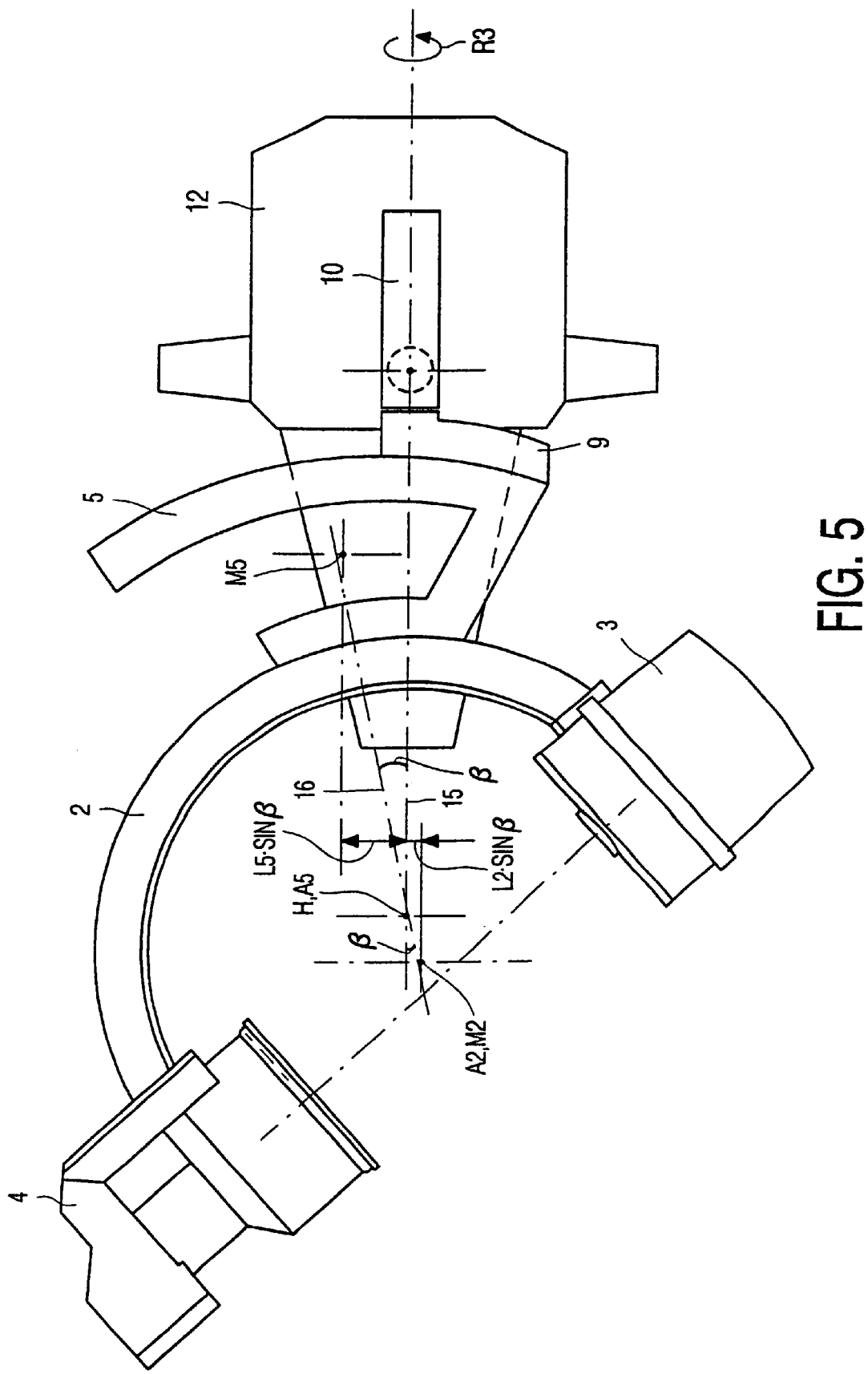

The FIGS. 4 and 5 are plan views of the X-ray device 1 according to the invention in further positions of the C-shaped arm 2 and the carriage 5. The FIGS. 4 and 5 show the propeller axis 15 with respect to which the guide 9 is rotatable in the direction of an arrow R3 and in the opposite direction. The propeller axis 15 extends horizontally. The C-shaped arm 2 is pivotable about a pivot axis A2 which extends transversely to the propeller axis 15. The mass center M2 of the C-shaped arm is situated on the pivot axis A2. In order to determine the mass M2 of the C-shaped arm 2, the entire mass which is pivotable relative to the carriage 5 should be taken into account. The carriage is tiltable about a tilting axis A5 which extends transversely to the propeller axis 15. The tilting axis A5 intersects the propeller axis 15 in the leverage point H. The mass center M5 of the carriage 5 is situated between the segmental arcs 6, 7 and the bridge portion 8. A leverage line 16 extends through the mass centers M2, M5 and the leverage point H. The mass centers M2, M5 are situated on the leverage line 16 to both sides of the leverage point H. In the position which is shown in FIG. 4, the leverage line 16 encloses an angle $\alpha$ relative to the propeller axis 15. The mass center M2 is situated at a distance L2 from the leverage point H and the mass center M5 is situated at a distance L5 from the leverage point H.

The C-shaped arm 2 exerts a turning moment around the propeller axis 10 in a direction which opposes that of the arrow R3, said turning moment being equal to the mass m2 of the C-shaped arm 2, multiplied by L2. sine $\alpha$. The carriage 5 exerts a turning moment around the propeller axis 10 in the direction indicated by the arrow R3; this turning moment is equal to the mass m5 of the carriage 5, multiplied by L5. sine $\alpha$. For the X-ray device 1 according to the invention it now holds that $$m2 \cdot L2 \cdot \sin(\alpha) m5 \cdot L5 \cdot \sin(\alpha)$$

or $$L2/L5 = m5/m2$$

This means that the ratio of the distance L2 between the mass center M2 of the C-shaped arm 2 and the leverage point H to the distance between the mass center M5 of the carriage 5 and the leverage point H is equal to the ratio of the mass m5 of the carriage 5 to the mass m2 of the C-shaped arm 2. The turning moments exerted around the propeller axis 15 by the C-shaped arm 2 and the carriage 5 cancel one another, so that the C-shaped arm 2 and the carriage 5 will not perform undesirable pivoting or tilting motions.

FIG. 5 shows another position of the carriage 5 and the C-shaped arm 2, the leverage line 16 now enclosing an angle $\beta$ relative to the propeller axis 15. The turning moment m2.L2.sin ($\beta$) exerted in the direction indicated by the arrow R3 about the propeller axis 15 by the C-shaped arm 2 is compensated by the turning moment m5.L5.sin ($\beta$) exerted about the propeller axis 15 in a direction opposing that of the arrow R3 by the carriage 5.

The turning moments exerted by the C-shaped arm 2 and the carriage 5 will cancel one another in any position of the C-shaped arm 2 and the carriage 5 due to the positions of the mass centers M2, M5 and the magnitude of the masses m2, m5.

If some friction exists between the C-shaped arm 2, the carriage 5 and the guide 9 it is allowed to deviate slightly from the optimum situation of the mass centers M2, M5 and the magnitude of the masses m2, m5 and the situation of the leverage point relative to the tilting axis, the effect of the self-stabilizing C-shaped arm 2 and the carriage 5 nevertheless being achieved.

It is possible for the propeller axis not to extend in parallel. It is also possible for the tilting axis and the pivot axis not to extend is parallel. It is also possible for the tilting axis and/or the pivot axis not to extend transversely of the propeller axis.

All references cited herein, as well as the priority document European Patent Application 98204239.2 filed Dec. 14, 1998, are incorporated herein by reference in their entirety and for all purposes to the same extent as if each individual publication or patent or patent application was specifically and individually indicated to be incorporated by reference in its entirety for all purposes.

What is claimed is:

1. An X-ray device comprising:
   a C-shaped arm, a first end of which supports an X-ray source and a second end of which supports an X-ray image pick-up device,
   a carriage which supports the C-shaped arm so that it is pivotable about a pivot axis, and
   a guide which supports the carriage so that it is tiltable about a tilting axis wherein
      the guide is rotatable about a propeller axis,
      the tilting axis extends at an angle relative to the propeller axis,
      a leverage point on the propeller axis is situated near the tilting axis,
      the mass center of the C-shaped arm is situated on the pivot axis,
      the mass centers of the C-shaped arm and of the carriage are situated on a leverage line which extends at least substantially through the leverage point,
      the mass centers of the C-shaped arm and of the carriage are situated to both sides of the leverage point, and and
      the ratio of the distance between the mass center of the C-shaped arm and the leverage point between the mass center of the carriage and the leverage point is substantially equal to the ratio of the mass of the carriage to the mass of the C-shaped arm.

2. An X-ray device as claimed in claim 1 wherein the leverage point is situated on the tilting axis and the leverage line.

3. An X-ray device as claimed in claim 1 wherein the tilting axis extends transversely the propeller axis.

4. An X-ray device as claimed in claim 1 wherein the propeller axis extends substantially horizontally.

5. An X-ray device as claimed in claim 1 wherein the pivot axis and the tilting axis extend in parallel.

6. The device of claim 2 wherein the tilting axis extends transversely to the propeller axis.

7. The device of claim 2 wherein the propeller axis extends substantially horizontally.

8. The device of claim 3 wherein the propeller axis extends substantially horizontally.

9. The device of claim 2 wherein the pivot axis and the tilting axis extend in parallel.

10. The device of claim 3 wherein the pivot axis and the tilting axis extend in parallel.

11. The device of claim 4 wherein the pivot axis and the tilting axis extend in parallel.

* * * * *